United States Patent [19]
Sinnreich

[11] 4,190,042
[45] Feb. 26, 1980

[54] SURGICAL RETRACTOR FOR ENDOSCOPES

[76] Inventor: Manfred Sinnreich, 160 Fort Hill Rd., Scarsdale, N.Y. 10583

[21] Appl. No.: 887,120

[22] Filed: Mar. 16, 1978

[51] Int. Cl.² .............................................. A61B 17/02
[52] U.S. Cl. ................................................... 128/20
[58] Field of Search ................ 128/20, 15, 3, 341, 128/343, 345, 130, 132 D, 303 R, 323, 361

[56] References Cited
U.S. PATENT DOCUMENTS

| | | | |
|---|---|---|---|
| 1,947,649 | 2/1934 | Kadavy | 128/303 R X |
| 2,204,275 | 6/1940 | Kesling | 128/345 |
| 2,863,444 | 12/1958 | Winsten | 128/20 |
| 3,515,129 | 6/1970 | Truhan | 128/20 |
| 3,683,905 | 8/1972 | Chaft | 128/130 |
| 4,038,978 | 8/1977 | Morris et al. | 128/130 |

Primary Examiner—Robert W. Michell
Assistant Examiner—Jeffrey W. Tayon
Attorney, Agent, or Firm—Charles E. Temko

[57] ABSTRACT

A surgical retractor for endoscopes and cystoscopes formed substantially entirely from resilient synthetic resinous material which in relatively unstressed condition forms a hook-like appendage at a distal end thereof, and which may be distorted to rectilinear configuration to fit within a channel in an endoscope barrel. The appendage may be of either endless or bifurcated configuration defining an enclosed area which is covered by a web-like membrane preventing the entry therebetween of any loose tissue which would otherwise be entrapped within the retractor when the same is withdrawn after use.

3 Claims, 5 Drawing Figures ern
SURGICAL RETRACTOR FOR ENDOSCOPES

BACKGROUND OF THE INVENTION

This invention relates generally to the field of surgical instrumentation, and more particularly to a flexible retractor particularly suited for use with endoscopic or cystoscopic devices commonly used for performing examinations or surgical procedures within body cavities, either natural or incised. Endoscopes and cystoscopes are characterized in the provision of an elongated barrel of relatively thin diameter forming a plurality of channels extending between proximal and distal ends, the latter being inserted into the cavity. Various elements are operated through each channel, one channel normally providing for illumination of the cavity, another a degree of vision into the cavity, while still others provide for control of specialized surgical tools performing specific procedural functions.

The function of holding loose tissue out of the way so that a procedure may be adequately viewed and performed is accomplished by a retractor, which in prior art constructions, has been in the form of a plurality of resilient metallic fingers which are spread relative to each other upon leaving the distal and other respective channel when the barrel is positioned within the cavity. When the retractive function is completed, the figures are resiliently compressed by the mouth of the channel, and are withdrawn therethrough.

The use of this structure has not been without complication. In some instances, a piece of tissue becomes caught between a pair of fingers as the same are withdrawn to cause unintentional lacerations. Sometimes the tissue is not readily dislodged, and it is difficult to withdraw the retractor into the channel prior to removing the entire device.

SUMMARY OF THE INVENTION

Briefly stated, the invention contemplates the provision of an improved flexible retractor of the class described which is formed as an integral molding of resilient synthetic resinous material. In place of individual resilient fingers, one embodiment of the retractor structure is in the form of a continuous loop which, in relatively unstressed condition, forms a retractive configuration without an opening into which tissue may enter. The area enclosed within the continuous loop is covered by a thin flexible membrane which is tensed upon the expansion of the loop to relatively unstressed condition, thereby preventing the fortuitous entry of a hanging loop or projecting piece of tissue in a direction substantially perpendicular to the plane of the loop. In another embodiment, separate integrally molded fingers are provided which are interconnected by a similar web.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENTS

Figure 1:
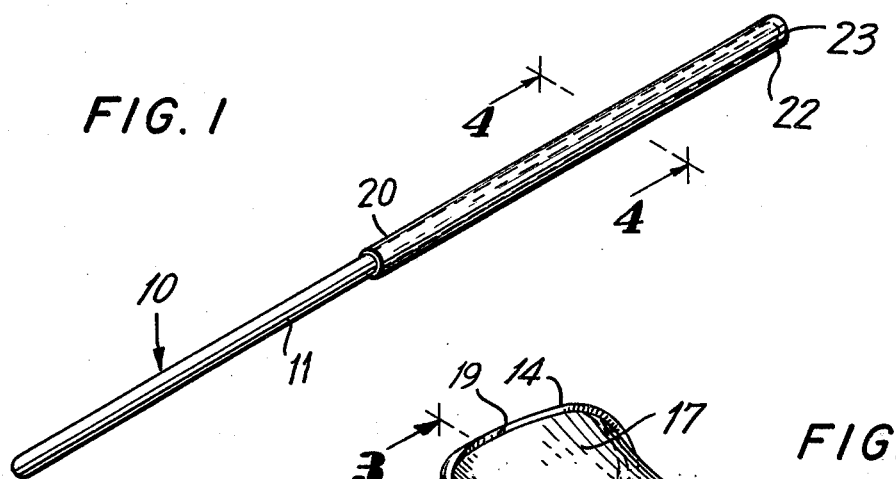
FIG. 1 is a fragmentary sectional view of a first embodiment of the invention, showing the same in relatively collapsed condition, and partially disposed within a channel in an endoscopic or cystoscopic device.

In accordance with the first embodiment of the invention, the device, generally indicated by reference character 10 is formed as a unitary molding of resilient synthetic resinous materials. Such materials are widely known in the art and may, for example, be of a type widely used in the molding of intrauterine contraceptive devices. Polyethylene is particularly suitable.

Figure 4:
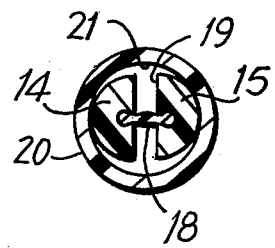
FIG. 4 is a sectional view as seen from the plane 4—4 in FIG. 1.
Figure 5:
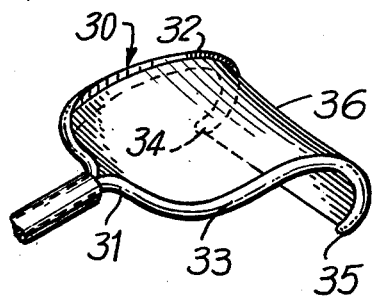
FIG. 5 is a perspective view of a second embodiment of the invention.

The device 10 includes an elongated rectilinear shaft 11 of generally circular cross-section, and a bifurcated member 12 which separates upon projection from an endoscope channel. In expanded condition, the member 12 includes a pair of base portions 13, first and second curvate portions 14 and 15, respectively, which are generally longitudinally oriented; and a third curvate portion 16 interconnecting the portions 14 and 15 and being generally transversely oriented, the members 13-16 inclusive defining the periphery of an enclosed area 17. The portions 13-16 inclusive, are of generally semicircular cross-section, as best seen in FIG. 4, and are interconnected by a thin flexible membrane 18 of material which interconnects the inner peripheral surfaces 19. This membrane may be as little as two-thousandths of an inch in thickness, and occupies negligible volume.

Figure 2:
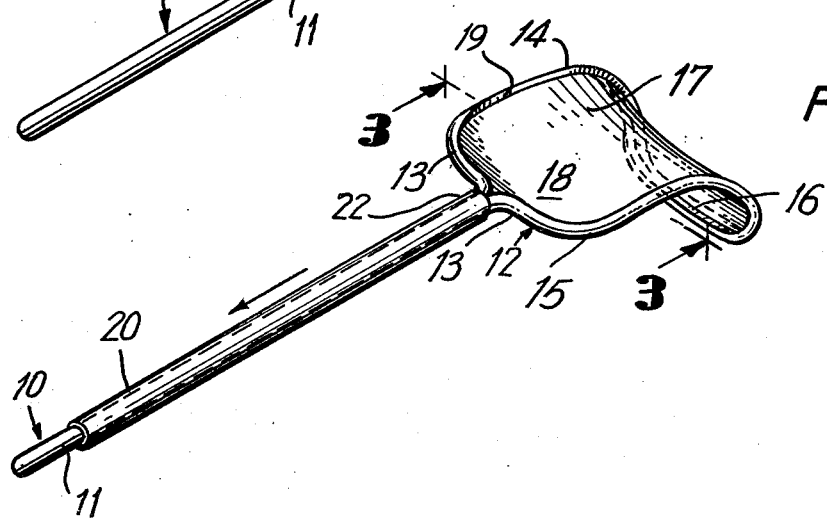
FIG. 2 is a similar fragmentary sectional view of the first embodiment in relatively extended condition in configuration for retraction.
Figure 3:
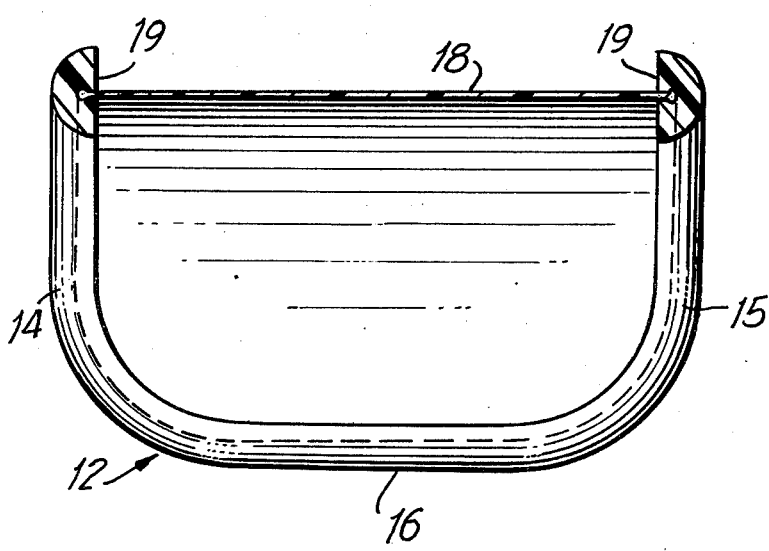
FIG. 3 is a transverse sectional view as seen from the plane 3—3 in FIG. 2.

Referring to FIGS. 1 and 2, reference character 20 designates the barrel of a known endoscope which defines a cylindrical channel 21 having a distal end 22 and a distal end edge 23.

In retracted condition, as shown in FIG. 1, the entire device may be disposed within the channel 21. Once the endoscope has been inserted into a body cavity, the retractor is extended to the position shown in FIG. 2, wherein the member 12 assumes a retractor configuration. As the retractor expands, the membrane 18 is tensed as shown in that Figure, and prevents the entry of any loose tissue within the cavity, so that when the retractor is ultimately withdrawn at the end of the procedure, there is no opportunity for such tissue to become pinched.

Turning now to the second embodiment of the invention, generally indicated by reference character 30, this embodiment differs from the first embodiment in the configuration of the bifurcated member 31 which includes first and second discrete segments 32 and 33, each terminating in a free end at 34 and 35, respectively. The web 36 extends between the segments 32 and 33, and performs a function similar to that in the principal embodiment.

I wish it to be understood that I do not consider the invention limited to the precise details of structure shown and set forth in this specification, for obvious modifications will occur to those skilled in the art to which the invention pertains.

I claim:

1. An improved collapsable surgical retractor comprising: a hollow barrel defining an elongated channel having proximal and distal ends; a unitary molding of resilient synthetic resinous material including an elongated rectilinear shaft member slidably disposed within said channel, a bifurcated member on a distal end of said shaft, selectively positionable within said channel and having a relatively unstressed configuration when positioned outwardly of said channel, said bifurcated member including a plurality of interconnected segments having inwardly and outwardly directed peripheral surfaces, and defining a hook-like appendage of substantial transverse width, and forming an angle with respect to the axis of said shaft member, said segments defining an at least partially enclosed area; and a thin web-like membrane interconnecting the inwardly directed surfaces of said bifurcated member, and extending over said enclosed area; whereby when said bifurcated member is positioned completely within said channel, it assumes a rectilinear configuration, and when extended outwardly past said distal end of said channel, said bifurcated member resiliently expands to relatively unstressed operative configuration, said membrane being thereby tensed to prevent the accidental entry of tissue into said enclosed area, and preventing the pinching of said tissue upon withdrawal of said bifurcated member within said channel.

2. A retractor in accordance with claim 1, further characterized in said bifurcated member defining a closed loop.

3. A retractor in accordance with claim 1, further characterized in said bifurcated member including a pair of discrete, generally parallel segments.

* * * * *